(12) United States Patent
Boix Borrás et al.

(10) Patent No.: US 10,487,117 B2
(45) Date of Patent: Nov. 26, 2019

(54) ANTIMICROBIAL PEPTIDE FOR NOSOCOMIAL INFECTIONS

(71) Applicants: UNIVERSITAT AUTONOMA DE BARCELONA, Bellaterra (Cerdanyola del Valles) (ES); UNIVERSITAT POMPEU FABRA, Barcelona (ES)

(72) Inventors: Ester Boix Borrás, Bellaterra (ES); Marc Torrent Burgas, Bellaterra (ES); David Andreu, Barcelona (ES)

(73) Assignees: UNIVERSITAT AUTONOMA DE BARCELONA, Bellaterra (Cerdanyola (ES); UNIVERSITAT POMPEU FABRA, Barcelona (ES)

( * ) Notice: Subject to any disclaimer, the term of this patent is extended or adjusted under 35 U.S.C. 154(b) by 0 days.

(21) Appl. No.: 15/747,934

(22) PCT Filed: Jul. 28, 2016

(86) PCT No.: PCT/EP2016/067989
§ 371 (c)(1),
(2) Date: Jan. 26, 2018

(87) PCT Pub. No.: WO2017/017177
PCT Pub. Date: Feb. 2, 2017

(65) Prior Publication Data
US 2018/0222943 A1    Aug. 9, 2018

(30) Foreign Application Priority Data
Jul. 30, 2015 (EP) .................................... 15179045

(51) Int. Cl.
| | | |
|---|---|---|
| *A61K 38/00* | (2006.01) | |
| *C07K 14/00* | (2006.01) | |
| *A61P 31/04* | (2006.01) | |
| *A61P 31/12* | (2006.01) | |
| *A61P 31/00* | (2006.01) | |
| *C12N 9/22* | (2006.01) | |

(52) U.S. Cl.
CPC ............ *C07K 14/001* (2013.01); *A61P 31/04* (2018.01); *C12N 9/22* (2013.01); *A61K 38/00* (2013.01); *Y02A 50/473* (2018.01); *Y02A 50/481* (2018.01)

(58) Field of Classification Search
CPC .......... A61K 38/00; A61P 31/04; A61P 31/12; A61P 31/00; C07K 14/00; C07K 14/001
USPC ..... 514/21.3, 2.8, 1.1, 2.3, 2.4, 3.3, 3.4, 3.5, 514/3.7, 4.2, 4.3, 4.4; 530/300, 324
See application file for complete search history.

(56) References Cited

PUBLICATIONS

Pulido et al, "Positional scanning library applied to the human eosinophil cationic protein/RNase3 N-terminus reveals novel and potent anti-biofilm peptides," European Journal of Medicinal Chemistry, 152: 590-599, May 25, 2018 (enclosed as pp. 1-32).*

Torrent et al, "Refining the Eosinophil Cationic Protein Antibacterial Pharmacophore by Rational Structure Minimization," Journal of Medicinal Chemistry, 54: 5237-5244, 2011.*

Nagant et al, "Identification of Peptides Derived from the Human Antimicrobial Peptide LL-37 Active against Biofilms Formed by Pseudomonas aeruginosa Using a Library of Truncated Fragment," Antimicrobial Agents and Chemotherapy, 56(11); 5698-5708, 2012.*

\* cited by examiner

*Primary Examiner* — Julie Ha
(74) *Attorney, Agent, or Firm* — Harness, Dickey & Pierce, P.L.C.

(57) ABSTRACT

A novel antimicrobial peptide is provided having an inhibitory effect on biofilms produced by biofilm-forming bacteria. The peptide is effective against wide range bacterial targets; generates no antimicrobial resistance; agglutinates bacteria cells enhancing the pathogen removal at the infectious focus; promotes biofilm eradication and prevents biofilm development. Compositions comprising the peptide are provided to treat and prevent infectious diseases, and for other uses such as the disinfection of medical and surgical materials.

15 Claims, 2 Drawing Sheets
Specification includes a Sequence Listing.

US 10,487,117 B2

ANTIMICROBIAL PEPTIDE FOR NOSOCOMIAL INFECTIONS

CROSS-REFERENCE TO RELATED APPLICATIONS

This application is a 371 U.S. National Stage of International Application No. PCT/EP2016/067989, filed Jul. 28, 2016, which claims the benefit of European Patent Application No. EP15179045.8, filed Jul. 30, 2015. The disclosures of the above applications are incorporated herein by reference.

FIELD OF THE INVENTION

The present invention relates to novel antimicrobial peptides having an inhibitory effect on biofilms produced by biofilm-forming bacteria. The invention includes inter alia methods of treating nosocomial infections and preventing the spread of the infections or contamination by the infection.

BACKGROUND ART

Nosocomial infection (also known as hospital-acquired infection) is an infection whose development is favored by a hospital environment, such as one acquired by a patient during a hospital visit or one developing among hospital staff.

Nosocomial infections can cause severe pneumonia and infections of the urinary tract, bloodstream and other parts of the body. Many types are difficult to attack with antibiotics, and antibiotic resistance is spreading to bacteria that can infect people outside the hospital. Among the categories of bacteria most known to infect patients are MRSA (methicillin-resistant *Staphylococcus aureus*), a Gram-positive bacterium, and *Acinetobacter baumannii*, which is Gram-negative. *Acinetobacter* bacteria are evolving and becoming immune to existing antibiotics, including even last-resource antibacterials such as polymyxins. Another growing threat is the drug-resistant, Gram-negative *Klebsiella pneumoniae*, which can cause severe pneumonia and infections of the urinary tract, bloodstream, and other parts of the body. The membrane structures of these bacteria make them difficult to attack with antibiotics, so that antibiotic resistance is spreading, often due to bacteria that can infect people outside the hospital.

For nosocomial pneumonia, specifically, the pathogens are primarily MRSA, and antibiotic-resistant Gram-negatives, of which *P. aeruginosa* is typically most common.

Antibiotics with coverage against Gram-positive and Gram-negative organisms, including *Pseudomonas*, should be empirically assayed and then tailored according to the susceptibility pattern of the isolated organisms. Two-drug combinations (e.g. an antipseudomonal beta-lactam with an aminoglycoside) are often used.

*P. aeruginosa*, as mentioned above, is a major nosocomial pathogen responsible for severe chronic and acute infection, particularly one of the most frequent causes of ventilator-associated pneumonia and catheter related bloodstream infections. It is the most common pathogen isolated from patients who have been hospitalized longer than 1 week. Patients with acquired-immune deficiency syndrome (AIDS), burn wounds and cystic fibrosis present a high risk of developing *P. aeruginosa* infections posing a serious clinical challenge with sepsis mortalities as high as 60% in immunocompromised patients.

The opportunistic pathogens causing nosocomial infections, such as *Pseudomonas aeruginosa*, once established within the host are able to form biofilms, a sine qua non feature for the development of a variety of chronic infections. They are also able to form biofilms on the inert surfaces of medical devices of internal and external use. Biofilms, defined as microbial communities attached to an abiotic surface, represent an additional challenge to antimicrobial therapies. Biofilm formation is induced by genotypic and phenotypic changes of the planktonic microorganisms, ensuing in a multi-layered cell cluster structure coated by an external polysaccharide matrix; composed of polysaccharides, proteins and extracellular DNA. Once organized in biofilm structures pathogenic bacteria become more resistant to antibiotic agents and immune system clearance, requesting a more elaborated strategy for a successful treatment of associated infections. Therefore, there is an urgent need to develop effective antimicrobial strategies against both planktonic and biofilm forms of these pathogens.

Antimicrobial proteins and peptides (AMPs) are proposed as new alternative candidates to current treatments for biofilm associated infections. AMPs are small, amphipathic, and frequently cationic molecules, characterized by rapid, potent and broad-spectrum action against microorganisms.

Human RNases have been studied as a new potential source for developing alternative antimicrobial agents. Human RNase 3, also known as eosinophil cationic protein (ECP), is a small highly cationic protein (pI~11) that is stored in the secondary granules of eosinophils. RNase 3 is secreted during the infection process where the protein exerts a high antimicrobial activity against a wide range of microorganisms, such as bacteria, viruses and parasites. Some ECP analogues have been studied with the aim of elucidating the amino acid residues with antimicrobial properties (Torrent M. et al. 2011).

Other antimicrobial peptides have been described as potent *P. aeruginosa* inhibitors. One such is LL-37, from the cathelicidin family, which presents a high interaction for the negatively charged bacterial membranes and LPS molecules and reported antimicrobial activity against planktonic *P. aeruginosa*. Furthermore, LL-37 is able to both inhibit *P. aeruginosa* biofilm formation and remove preformed *P. aeruginosa* biofilms (Nagant C. et al. 2012).

Secondly, the hybrid peptide cecropin A (1-7)-melittin(2-9), named CA-M, and resulting from the juxtaposition of residues (1-7) of cecropin A to residues (2-9) of melittin, is a potent antimicrobial against a wide variety of microorganisms. CA-M is a small, amphipathic and cationic peptide, with a high affinity to bacterial negatively charged membranes, exerting its antimicrobial action by pore formation (Saugar J. M. et al. 2006).

The beta-boomerang WY-12 peptide, adopts a particular β-stranded secondary structuration that resembles a boomerang upon LPS interaction and combines antimicrobial activity with LPS affinity (Bhunia A. et al. 2009).

Lastly, the human parotid secretory derived peptide GL-13 is devoid of antimicrobial activity but is able to induce *P. aeruginosa* agglutination (Gorr S. U. et al. 2008).

In spite of the existence of the above-mentioned potentially antimicrobial peptides, eradication of established biofilm communities of pathogen species is one of the pending challenges for the development of new antimicrobial agents. In particular, as already noted above, *P. aeruginosa* is of serious concern among nosocomial pathogens, for its tendency to form organized microbial communities posing enhanced resistance to conventional antibiotics.

BRIEF DESCRIPTION OF THE INVENTION

One problem to be solved by the present invention may be seen as related to the provision of antimicrobial agents with enhanced antimicrobial properties.

The solution is based on the provision of a peptide which is effective against wide range bacterial targets; generates no antimicrobial resistance; agglutinates bacteria cells enhancing the pathogen removal at the infectious focus; promotes biofilm eradication and prevents biofilm development. Thus, it is believed that no prior art describes a peptide with the structural features defined herein, which combines an enhanced antimicrobial activity paired to a high LPS binding and the capability to agglutinate bacterial community cells, together with the capability to totally eradicate established biofilms, and showing all these activities at low doses (concentrations).

The invention provides a peptide with potent antimicrobial efficacy. In particular, the peptide proved highly effective against both planktonic and established biofilms of *P. aeruginosa*. The peptide mechanism was evaluated by means of a variety of functional methodologies. The antimicrobial properties of the peptide were compared with previously characterized antimicrobial peptides, as cathelicidin LL-37 with reported antibiofilm activity, the hybrid peptide cecropin-melittin with a high potency against *P. aeruginosa*, the beta-Boomerang peptide WY-12 with high affinity for the LPS moiety, and the GL-13 peptide, proven to agglutinate *Pseudomonas* cells. Remarkably, the comparative results demonstrate that the peptide of the invention was the only peptide able to totally remove established biofilms through bacterial killing and agglutination, highlighting the huge potential of the peptide for pathogen biofilm eradication.

Accordingly, a first aspect of the invention relates to a peptide consisting of the amino acid sequence: $X_1$-$Pro_2$-$X_3$-$X_4$-$X_5$-$Ala_6$-$Gln_7$-$Trp_8$-$Phe_9$-$Ala_{10}$-$Ile_{11}$-$Gln_{12}$-$His_{13}$-$Ile_{14}$-$X_{15}$-$Pro_{16}$-$X_{17}$-$X_{18}$-$X_{19}$-$Ala_{20}$-$Met_{21}$-$X_{22}$-$Ala_{23}$-$Ile_{24}$-$X_{25}$-$X_{26}$-$Tyr_{27}$-$Arg_{28}$-$Trp_{29}$-$Arg_{30}$-$X_{31}$-$NH_2$
wherein:

$X_1$, $X_5$, $X_{17}$, $X_{22}$ are amino acids selected from the group consisting of Arg and Lys, $X_3$ is an amino acid selected from the group consisting of Phe, Leu, Ile and Val, $X_4$ is an amino acid selected from the group consisting of Thr, Phe and Ile, $X_{15}$ is any amino acid, $X_{18}$ is an amino acid selected from the group consisting of Thr, Ser, Gln and Asn, $X_{19}$ is an amino acid selected from the group consisting of Ile, Leu and Val, $X_{25}$ is an amino acid selected from the group consisting of Asn, His, and Lys, $X_{26}$ is an amino acid selected from the group consisting of Asn, Lys and Trp, and $X_{31}$ is either absent or from one to nine amino acids selected from the group consisting of Asn, Gln, Ser and Thr.

As a second aspect, the invention provides a peptide consisting of an amino acid sequence which has a 90% identity to sequence SEQ ID NO: 1, wherein the peptide has antimicrobial activity and has an inhibitory effect on biofilm formation by a biofilm-producing microorganism.

The term "% identity" is well-understood in the art as the amount of characters which match exactly between two different sequences.

The peptide has antimicrobial activity and has an inhibitory effect on biofilm formation by a biofilm-producing microorganism. Such activities are testable by a well-established assay, e.g. the assays depicted in Example 1 and 7.

The method to evaluate the antimicrobial activity generally includes contacting a test peptide with a microbe under conditions sufficient for antimicrobial activity, and detecting a change in growth or proliferation of the microbe as compared to the growth or proliferation of the microbe prior to contacting with the test peptide. The antimicrobial activity of the peptides can be determined by standard methods known to those of skill in the art, such as "minimal inhibitory concentration (MIC)" assay described in the present examples, whereby the lowest concentration at which there are no remaining colony forming units, or no change in OD is observed for a given period of time in a growth media culture, is recorded as MIC. The antibiofilm activity can be determined by e.g. the assays described in the examples, measuring the "minimal biofilm eradication concentration" (MBEC).

"Antimicrobial", as used herein means that the peptides of the present invention inhibit, prevent, or destroy the growth or proliferation of microbes such as bacteria, fungi, viruses, parasites or the like. Antimicrobial can also be generally referred as disinfectant, antiseptic, or antibiotic.

It is understood that the peptide is "isolated" in the meaning that is substantially free of e.g. proteins, lipids, nucleic acids. Furthermore, the peptide is not a naturalocurring peptide, since is the result of extensive studies based on the RNase 3 sequence (which is natural occurring), and an engineering process of cut-and-paste and of selection of amino acids. The resulting peptide with the unique amino acid sequence is not found in nature.

Furthermore, even though the peptide has been designed with the RNAse 3 sequence as starting point, the peptide has surprising advantages in respect of the RNase 3 due to the specific deletion and selection of the amino acids conforming the peptide amino acid. In the process of design of the peptide of the invention, there were peptides that did not display the antimicrobial and antibiofilm activities displayed by the peptide of the invention. This is the case of the peptide ECP(7-13)(32-36) with sequence SEQ ID NO: 7.

In the same way, the prior art describes other peptides derived from RNase 3, such as the peptides disclosed in Torrent M. et al. 2011, but they have worse performance and features in respect of the peptide of the invention.

Third and fourth aspects relate to the use of the peptide of the invention as antimicrobial agent and as antibiofilm agent.

A fifth aspect relates to the peptide of the invention for use as a medicament. It is well-known that the biological properties found on the peptide of the invention such as inhibition of bacteria growth, bacteria agglutination, LPS binding and antibiofilm effect have been associated with a clinical effect in infectious disease treatment. Thus, molecules that have the whole above properties are potential antibiotics.

A sixth aspect relates to the peptide for use in the treatment and/or prevention of infectious diseases.

A seventh aspect relates to a pharmaceutical composition comprising the peptide as defined above, and a pharmaceutical acceptable carrier, diluent or excipient.

Eighth and ninth aspects relate to a composition comprising the peptide and a carrier or diluent, and an item impregnated with, coated in or covered by said composition, wherein the item is selected from the group consisting of: a medical device, medical instrument, medical implement, prosthetic, implantable device or material, wound dressing and a biologically compatible material.

Finally, another aspect of the invention relates to an antibody specific for peptide as defined above.

The detailed description and examples shown below are presented for the purposes of providing those skilled in the art with a sufficiently clear and complete explanation of this invention, but should not be considered limitations on the essential aspects contemplated therein, as presented in earlier sections of this description.

DETAILED DESCRIPTION OF THE INVENTION

In this description, the nomenclature or symbolic representation of the amino acids may be given by either the standard 3-letter abbreviation or the standard single letter code. The peptide of the invention is also called in this description as RN3(5-17P22-36).

First and Second Aspects

Peptide Structure

As discussed above, the peptide of the invention consists of the following amino acid sequence:

$X_1$-$Pro_2$-$X_3$-$X_4$-$X_5$-$Ala_6$-$Gln_7$-$Trp_8$-$Phe_9$-$Ala_{10}$-$Ile_{11}$-$Gln_{12}$-$His_{13}$-$Ile_{14}$-$X_{15}$-$Pro_{16}$-$X_{17}$-$X_{18}$-$X_{19}$-$Ala_{20}$-$Met_{21}$-$X_{22}$-$Ala_{23}$-$Ile_{24}$-$X_{25}$-$X_{26}$-$Tyr_{27}$-$Arg_{28}$-$Trp_{29}$-$Arg_{30}$-$X_{31}$-$NH_2$.

$X_1$, $X_5$, $X_{17}$, $X_{22}$ are amino acids selected from the group consisting of Arg and Lys. In a particular embodiment, all the amino acids $X_1$, $X_5$, $X_{17}$, $X_{22}$ are Arg. In another particular embodiment, at least one amino acid from $X_1$, $X_5$, $X_{17}$, $X_{22}$ is Lys.

$X_3$ is an amino acid selected from the group consisting of Phe, Leu, Ile and Val.

In a particular embodiment, $X_3$ is Phe.

$X_4$ is an amino acid selected from the group consisting of Thr, Phe and Ile.

Preferably, $X_4$ is Thr. More preferably, $X_4$ is Ile.

$X_{15}$ is any amino acid. In a particular embodiment, $X_{15}$ is a polar amino acid, and preferably, is Ser.

$X_{18}$ is a polar amino acid, and preferably is Thr. Polar amino acids are Thr, Ser, Gln and Asn.

$X_{19}$ is an amino acid selected from the group consisting of Ile, Leu and Val. In a particular embodiment, $X_{19}$ is Ile.

$X_{25}$ is preferably a Asn, but can be a cationic amino acid selected from the group consisting of His and Lys.

$X_{26}$ is an amino acid selected from the group consisting of Asn, Lys and Trp.

In a particular embodiment, $X_{25}$ and $X_{26}$ are Asn. In another particular embodiment, at least one amino acid from $X_{25}$ and $X_{26}$ is Lys.

$X_{31}$ is either absent or from one to nine amino acids selected from the group consisting of Asn, Gln, Ser and Thr.

Combinations of the above-discussed embodiments are also encompassed by the present invention.

In a particular embodiment, the peptide has antimicrobial activity and has an inhibitory effect on biofilm formation by a biofilm-producing microorganism. Such activities are testable by a well-established assay, as discussed above.

Another aspect of the invention is a peptide consisting of an amino acid sequence which has a 90% identity to sequence SEQ ID NO: 1, wherein the peptide has antimicrobial activity and has an inhibitory effect on biofilm formation by a biofilm-producing microorganism. The activities are testable as discussed above.

In a particular embodiment of the invention, the peptide has the amino acid sequence SEQ ID NO: 1 (RPF-TRAQWFAIQHISPRTIAMRAINNYRWR-NH2).

It is also within the scope of the invention a pharmaceutically acceptable salt of the peptide. A "pharmaceutically acceptable salt" refers to a salt that retains the desired biological activity of the parent compound and does not impart any undesired toxicological effects. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Disclosed peptides are produced by chemical synthetic procedures. Chemical peptide synthesis is a rapidly evolving area in the art, and methods of solid phase peptide synthesis are well-described in the following reference: Kowalczyk W. et al., 2011. Disclosed peptides may also be utilized as research reagents and materials for discovery of treatments and diagnostics for human/animal diseases.

Peptide Features

The peptide is able to perform the same bactericidal effects, i.e. a strong antimicrobial activity against the Gram-negative P. aeruginosa, as its parental protein RNase 3 at similar low concentrations. Interestingly, the peptide displays a significant enhanced activity respect to the parental protein against P. aeurginosa biofilm communities. Furthermore, the antimicrobial activity of the peptide of the invention is higher than the recorded for the selected reference antimicrobial peptides.

Interestingly, the peptide of the invention mediates its antimicrobial action through bacterial agglutination against Gram-negative bacteria. In the Examples, it is showed that the peptide is able to agglutinate P. aeruginosa at lower concentrations than RNase 3. Moreover, the agglutinating activity of both RNase 3 and RN3(5-17P22-36) against P. aeruginosa is similar to the activity displayed by the potent agglutinating peptide GL-13. However, the GL-13 peptide does not display a detectable antimicrobial activity.

Another key feature to mediate the peptide activity against Gram negative bacteria and to facilitate the antimicrobial action is the ability to interact with the negatively charged surfaces of bacteria, in particular to the outer membrane LPS. Although, LPS could pose a hydrophilic barrier to hydrophobic antimicrobial compounds, several AMPs are able to use the LPS molecule as a first point of interaction to exert their bactericidal activities. As shown in the Examples, the peptide of the invention displays a high affinity towards LPS at low concentrations.

After the interaction with the negatively charged molecules of the bacterial cell envelopes, antimicrobial peptides exert their bactericidal action by producing the loss of membrane potential and permeabilizing the cytoplasmic membrane inducing the cell lysis and death. The present results show that the peptide displays even a higher membrane depolarizing effect in comparison to CA-M, which was previously reported to display a high depolarization activity against a wide range of Gram-positive and negative bacteria. Besides, antimicrobial peptides LL-37 and WY-12 present lower maximum depolarization percentages against *P. aeruginosa*.

The present results highlight that the peptide of the invention is highly active against the planktonic form of *P. aeruginosa*.

As discussed above, however, when bacteria are organized in a biofilm community they acquire a great enhancement of their resistance towards antimicrobial agents. Biofilms constitute a complex structure where bacteria are coated by a dense layer of extracellular matrix. This matrix is mainly composed by polysaccharides and is generally referred as the exopolysaccharide (EPS). Gram-negative EPS is mostly composed by extracellular matrix polysaccharides, such as LPS, proteoglycans and extracellular DNA; most of these molecules are largely negatively charged inhibiting the diffusion of antimicrobials by charge repulsion and steric hindrance. Therefore, it has been described that classic antibiotic compounds require between 10- to 1000-fold higher concentrations against biofilm to be as effective as against planktonic cells.

Remarkably, the present findings demonstrate that the peptide of the invention exhibits a high antibiofilm activity being able to drastically reduce the viability of the cell population and disperse most of the established biofilm; showing better results than the reference tested peptides. It is relevant to note that the prior art concerning the parental RNase 3 is silent about RNase antibiofilm properties. The antimicrobial peptides LL-37, CA-M and WY-12, that exhibit a high antimicrobial activity against planktonic *P. aeruginosa*, are unable to totally eradicate the established biofilm, showing also lower depolarization and permeabilization activities. Interestingly, the peptide of the invention not only retains a high antimicrobial action but in addition can better overcome the complexity of the biofilm EPS barrier and reach the encased bacterial membranes. Most importantly, the peptide of the invention achieves the total eradication of the established biofilm mediated by membrane disruption and bacterial killing.

Thus it is believed that no prior art describes a peptide with the structural features defined above, which combines an enhanced antimicrobial activity paired to a high LPS binding and the capability to agglutinate bacterial community cells, together with the capability to totally eradicate established biofilms, and all activities at low concentrations.

In summary, the peptide of the invention presents the following relevant characteristics: antimicrobial action on planktonic bacterial cells; agglutinating activity on planktonic bacterial cells; LPS binding affinity; ability to depolarize bacterial cells membranes; membrane permeabilization activity; and antibiofilm action. Regarding antibiofilm action, remarkably, the only tested AMP that could reduce the bacterial population on the established biofilm on its totality was the peptide of the invention, showing better results than the parental protein RNase 3. The peptide was able to totally disperse the cell community layer. On the other hand, the reference peptides LL-37, CA-M, WY-12 and GL-13 showed moderate effects being able to disperse from 30 to 50% of the total biofilm. Moreover, the biofilm eradication activity of all the tested reference peptides was well above the maximum concentration tested (50 µM), except for the peptide of the invention which was able to eradicate the biofilm close to 50 µM.

Peptide Modifications

Minor modifications of the primary amino acid sequence of the peptide of the invention may result in peptides that have substantially equivalent activity as compared to the specific peptides described herein. Such modifications may be deliberate, as by site-directed mutagenesis, or may be spontaneous. All of the peptides produced by these modifications are included herein as long as the biological activity of the original peptide still exists.

Examples of modifications include variants of the peptide molecule brought about by, homologous substitution of one or more amino acid residues as will be appreciated by those skilled in the art, reversal of the sequence, or partial or complete replacement of component amino acids with compositionally identical enantiomers (D- vs L-amino acids).

The peptide can be synthesized using L amino acids, however, all D forms of the peptides can be synthetically produced. In addition, C-terminal derivatives can be produced, such as C-terminal methyl esters and C-terminal amidates, in order to increase the antimicrobial activity of a peptide of the invention. The peptide can be synthesized such that the sequence is reversed whereby the last amino acid in the sequence becomes the first amino acid, and the penultimate amino acid becomes the second amino acid, and so on. It is well known that such reversed peptides usually have similar antimicrobial activities to the original sequence.

Generally, the peptide of the invention includes naturally occurring amino acids. They consist of the 20 genetically encoded amino acids Ala, Arg, Asn, Asp, Cys, Gln, Glu, Gly, His, Ile, Leu, Lys, Met, Phe, Pro, Ser, Tyr, Thr, Trp, Val, and 2 which are incorporated into proteins by unique synthetic mechanisms: Sec (selenocysteine, or U) and Pyl (pyrrolysine, O). These are all L-stereoisomers.

Modifications include "conservative amino acid substitutions" in which one amino acid is substituted with an amino acid having a similar side chain. Examples of similar side chain amino acids, are basic side chain amino acids (e.g., lysine, arginine, histidine), acidic side chain amino acids (e.g., aspartic acid, glutamic acid), non polar side chain amino acids (e.g., glycine, alanine, valine, leucine, isoleucine, proline, phenylalanine, methionine, tryptophan), uncharged polar side chain amino acids (e.g., aspargine, glutamine, serine, threonine, tyrosine, cysteine), branched side chain amino acids (e.g., threonine, leucine, valine, isoleucine) and aromatic side chain amino acids (e.g., tyrosine, phenylalanine, tryptophan, histidine). "Homologous amino acid substitutions" are also included in which an amino acid is substituted with homologous amino acids, such as replacement of phenylalanine with tyrosine, pyridylalanine, or homophenylalanine, and replacement of leucine with valine, or vice versa.

Furthermore, the peptide of the invention can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like.

"Amino acid mimetics" refers to chemical compounds that have a structure different from the general chemical structure of an amino acid, but which functions in a manner similar to a naturally occurring amino acid. Examples of unnatural amino acid residues are Nle (Norleucine), Nal (beta-2-naphthylalanine), D-Nal (beta-2-naphthyl-D-alanine), D-Arg, D-Trp, D-Phe and D-Val.

Mimetics of acidic amino acids can be generated by substitution by, e.g., non-carboxylate amino acids while maintaining a negative charge; (phosphono) alanine; sulfated threonine. Carboxyl side groups (e.g., aspartyl or glutamyl) can also be selectively modified by reaction with carbodiimides (R'—N—C—N—R') such as, e.g., 1-cyclohexyl-3(2-morpholin-yl-(4-ethyl) carbodiimide or I-ethyl-3 (4-azonia-4,4-dimetholpentyl) carbodiimide. Aspartyl or glutamyl can also be converted to asparaginyl and glutaminyl residues by reaction with ammonium ions.

Mimetics of basic amino acids can be generated by substitution with, e.g., (in addition to lysine and arginine) the amino acids ornithine, or citrulline. Asparaginyl and glutaminyl residues can be deaminated to the corresponding aspartyl or glutamyl residues.

Arginine residue mimetics can be generated by reacting arginyl with, e.g., one or more conventional reagents, including, e.g., phenylglyoxal, 2,3-butanedione, 1,2-cyclohexanedione, or ninhydrin, preferably under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitrobenzenesulfonic acid, O-methylisourea, 2,4, pentanedione, and transamidase-catalyzed reactions with glyoxylate. Mimetics of methionine can be generated by reaction with, e.g., methionine sulfoxide. Histidine residue mimetics can be generated by reacting histidyl with, e.g., diethylprocarbonate or para-bromophenacyl bromide. Other mimetics include, e.g., those generated by hydroxylation of lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

Also included is the use of N-methylated analogs, including the use of αN-methylation or L-amino acids (preferably methylated amino acids) exclusively or partially during synthesis such that the resulting peptides will have purely αN-methylated amide bonds or partially αN-methylated or alternating αN-methylated and non-αN-methylated amide bonds. With modified amide bonds such that at least one of the amide bonds in the peptide back-bone is N-methylated, the peptide does not form beta-sheet conformation.

Thus, in a particular embodiment, one or more amino acids of the peptide are N-methylated.

Conservative variations are also encompassed by the present invention. "Conservative variation" as used herein denotes the replacement of an amino acid residue by another, biologically similar residue. Examples include, but are not limited to, the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic for aspartic acids, or glutamine for asparagine, and the like. Neutral hydrophilic amino acids that can be substituted for one another include asparagine, glutamine, serine and threonine.

In another aspect, a peptide of the present invention is a pseudopeptide. Pseudopeptides or amide bond surrogates refers to peptides containing chemical modifications of some (or all) of the peptide bonds, such as modifications with amide nitrogen, amide carbonyl, or complete replacement of the amide bond. The amide bond can advantageously be replaced by similar length bridges known to those skilled in the art, such as: —CH2S—, —CH=CH—, —CH2NH—, —CSNH2-, or COCH2-. Individual residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH2- for —C(=O)—NH—), aminomethylene (CH2-NH), ethylene, olefin (CH=CH), ether (CH2-O), thioether (CH2-S), tetrazole (CN4-), thiazole, retroamide, thioamide, or ester.

A component of the peptide of the invention can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, referred to as the D-amino acid, but which can additionally be referred to as the R- or S-form.

Whether completely or partially non-peptide, peptidomimetics according to this invention provide a spatial arrangement of reactive chemical moieties that closely resembles the three-dimensional arrangement of active groups in the peptide on which the peptidomimetic is based. As a result of this similar active-site geometry, the peptidomimetic has effects on biological systems that are similar to the biological activity of the peptide.

The invention also embraces post-translational modifications introduced by chemical or enzyme-catalyzed reactions, as are known in the art. Such post-translational modifications can be introduced prior to partitioning, if desired. Also, functional equivalents may comprise chemical modifications such as ubiquitination, labeling (e.g., with radionuclides, various enzymes, etc.), pegylation (derivatization with polyethylene glycol), or by insertion (or substitution by chemical synthesis) of amino acids (amino acids) such as ornithine, which do not normally occur in human proteins.

Preferably, the chemical modification(s) confer(s) or improve(s) desirable attributes of the peptide but does not substantially alter or compromise the biological activity thereof. Desirable attributes include but are limited to increased shelf-life; enhanced serum or other in vivo stability; resistance to proteases; and the like. Such modifications include by way of non-limiting examples N-terminal acetylation, glycosylation, and biotinylation.

Peptides with N-terminal alkylations and C-terminal esterifications are also encompassed within the present invention. Functional equivalents also comprise glycosylated and covalent or aggregative conjugates formed with the same molecules, including dimers or unrelated chemical moieties. Such functional equivalents are prepared by linkage of functionalities to groups which are found in fragment including at any one or both of the N- and C-termini, by means known in the art. In some embodiments, the peptides according to the present invention are modified by N-terminal acetylation of the most N-terminal amino acid. In some embodiments the peptides according to the present invention are modified by C-terminal amidation. In one embodiment such modification increases the stability of the peptides. In one embodiment, the carboxy terminus of said peptide or MSH-analogue as defined herein above is —C(=O)—B1, wherein B1 is selected from OH, NH2, NHB2, N(B2)(B3), OB2, and B2, and wherein B2 and B3 are independently selected from optionally substituted C1-6 alkyl, optionally substituted C2-6 alkenyl, optionally substituted C6-10 aryl, optionally substituted C7-16 aralkyl, and optionally substituted C7-16 alkylaryl.

Sterically similar compounds may be formulated to mimic the key portions of the peptide structure and that such compounds may also be used in the same manner as the peptides of the invention. This may be achieved by techniques of modelling and chemical designing known to those of skill in the art. For example, esterification and other alkylations may be employed to modify the amino terminus of e.g a di-arginine peptide backbone, to mimic a tetra peptide structure. It will be understood that all such sterically similar constructs fall within the scope of the present invention.

Finally, nanodelivery is used to ensure bioavailability of the peptide, e.g. by PEG scaffold nanodelivery and/or dendrimeric (branched) presentation. For PEGylation and branched versions, one (usually internal) amino acid of the sequence is mutated to a suitable multifunctional residue.

Third, Four, Eighth and Ninth Aspects—Use as Antimicrobial and Antibiofilm Agent, and use in the Disinfection of Medical and Surgical Devices As discussed above, an aspect of the invention is the use of the peptide as antimicrobial agent.

Another aspect of the invention is the use of the peptide as antibiofilm agent.

In a particular embodiment, the peptide is used in food preservation.

A particular embodiment of said aspects is the use of the peptide in the disinfection of medical and surgical materials, i.e. to protect medical material from colonization with pathogens and avoid and/or treat biofilm formation. Thus, the peptide of the invention can be used as material coating (medical and surgical devices) and for surface cleaning and sterilization (in the form of detergents, or disinfectants).

To this end, the invention also provides a composition comprising the peptide, and a carrier or diluent, to be use preferably in the above mentioned applications.

As discussed, and aspect of the invention is an item impregnated with, coated in or covered by a composition comprising the peptide, wherein the item is selected from the group consisting of: a medical device, medical instrument, medical implement, prosthetic, implantable device or material and wound dressing. Another aspect of the invention is a biologically compatible material selected from the group consisting of plastic, metal, cement, glue, composite, tissue scaffold and wound dressing incorporating or impregnated with a composition comprising the peptide.

Fifth and Sixth Aspects—Medical Use

As discussed, an aspect of the invention is the peptide for use as a medicament. Particularly, the peptide is used in the treatment and/or prevention of infectious diseases. More particularly, the infectious disease is selected from the group consisting of a bacterial, a viral, a parasitic and a fungal disease. This aspect can be alternatively formulated as the use of the peptide as defined in the first aspect for the manufacture of a pharmaceutical product, a medicament or a veterinary product, for the prevention and/or treatment of infectious diseases. This may be also alternatively formulated as a method for the prevention and/or treatment of an infectious disease in a mammal, including a human, comprising administering to said mammal in need thereof an effective amount of the peptide as defined in the first aspect of the invention More particularly, the infectious disease is a nosocomial infection. The term "nosocomial infection" is well known in the art and applies to any disease contracted by a patient while under medical care. The term "nosocomial" is synonymous with hospital-acquired. Nosocomial infections are infections that have been caught in a hospital and are potentially caused by organisms that are resistant to antibiotics. A nosocomial infection is specifically one that was not present or incubating prior to the patient's being admitted to the hospital, but occurring within 72 hours after admittance to the hospital. Non-limiting examples of nosocomial infections are infections caused by *Klebsiella pneumoniae, Escherichia coli, Pseudomonas aeruginosa, Staphylococcus aureus, Acinetobacter baumannii, Candida albicans, Aspergillus*, Respiratory Syncytial Virus, Rotavirus, Hepatitis C virus genotype 1b, and HIV virus.

In a particular embodiment, the infectious disease is a bacterial disease. More particularly, the infectious disease is caused by a Gram negative bacterial pathogen. More particularly, the gram negative pathogen is selected from the group consisting of: *Pseudomonas, Escherichia coli, Acinetobacter, Salmonella* and *Klebsiella*.

In another particular embodiment, the infectious disease is caused by a Gram positive bacterial pathogen. More particularly, the Gram positive pathogen is selected from the group consisting of: *Staphylococcus, Streptococcus, Propionibacterium, Enterococcus, Bacillus, Micrococcus* and *Listeria*.

In a more particular embodiment, the pathogen is selected from the group consisting of: *Pseudomonas aeruginosa, Escherichia coli, Klebsiella*, multiresistent *Acenitobacter, Acinetobacter baumanii, Staphylococcus aureus, Micrococcus luteus, Enterococcus faecium, Staphyloccocus xylosus, Staphyloccocus lugdunensis, Staphyloccocus schleiferi, Stapylococcus caprae, Staphylococcus epidermidis, Staphylococcus saprophyticus, Staphylococcus warneri, Staphylococcus hominis*, Methicillin-resistant *Staphylococcus aureus* (MRSA), *Enterococcus faecalis*, Vancomycin-resistant *Enterococcus* (VRE), *Propionibacterium acnes, Bacillus cereus, Bacillus subtilis, Listeria monocytogenes, Streptococcus pyrogenes, Streptococcus salivarius, Streptococcus mutans, Streptococcus pneumonia*, and *Salmonella enteritidis* ssp *Typhimurium*.

More particularly, the pathogen is selected from the group consisting of: *Pseudomonas aeruginosa* (Gram negative), *Escherichia coli* (Gram negative), *Klebsiella* (Gram negative), multiresistent *Acenitobacter* (Gram negative), *Acinetobacter baumanii* (Gram negative), *Staphylococcus aureus* (Gram positive), *Micrococcus luteus* (Gram positive), and *Enterococcus faecium* (Gram positive).

In particular, the peptide is used as antimicrobial and antibiofilm agent for topical treatment (wound healing, epithelial infection, etc).

Seventh Aspect—Pharmaceutical Compositions

As discussed above, the invention also provides a pharmaceutical composition comprising the peptide, and a pharmaceutical acceptable carrier, diluent or excipient.

As used herein "pharmaceutically acceptable carrier" includes any and all solvents, dispersion media, coatings, antibacterial and antifungal agents, isotonic and absorption delaying agents, and the like that are physiologically compatible. In one aspect, the carrier is suitable for parenteral administration. Alternatively, the carrier can be suitable for intravenous, intraperitoneal or intramuscular administration. In another aspect, the carrier is suitable for oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is compatible with the active compound, use thereof in the pharmaceutical compositions is contemplated. Supplementary active compounds can also be incorporated into the compositions.

In prophylactic applications, pharmaceutical compositions or medicaments are administered to a patient susceptible to, or otherwise at risk of a disease or condition {i.e., as a result of bacteria, fungi, viruses, parasites or the like) in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. In therapeutic applications, compositions or medicaments are administered to a patient suspected of, or already suffering from such a disease or condition in an amount sufficient to cure, or at least partially arrest, the symptoms of the disease or condition (e.g., biochemical and/or histologic), including its complications and intermediate pathological phenotypes in development of the disease or condition. An amount adequate to accomplish therapeutic or prophylactic treatment is defined as a therapeutically- or prophylactically-effective dose. In both prophylactic and therapeutic regimes, agents are usually administered in several dosages until a sufficient response has been achieved.

The pharmaceutical composition of the present invention should be sterile and fluid to the extent that the composition is deliverable by syringe. In addition to water, the carrier can be an isotonic buffered saline solution, ethanol, polyol (for example, glycerol, propylene glycol, and liquid polyethylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound can be orally administered, for example, with an inert diluent or an assimilable edible carrier.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins. Co-administration can be achieved by using the components as a mixture or as linked molecules obtained by chemical crosslinking or expression as a fusion protein. Alternatively, transdermal delivery can be achieved using a skin patch or using transferosomes.

Pharmaceutical compositions of the invention also can be administered in combination therapy, i.e., combined with other agents. For example, in treatment of bacteria, the combination therapy can include a composition of the present invention with at least one agent or other conventional therapy.

A composition of the present invention can be administered by a variety of methods known in the art. The route and/or mode of administration vary depending upon the desired results. The phrases "parenteral administration" and "administered parenterally" mean modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. The peptide of the invention can be administered parenterally by injection or by gradual infusion over time. The peptide can also be prepared with carriers that protect the compound against rapid release, such as a controlled release formulation, including implants, transdermal patches, and microencapsulated delivery systems. Further methods for delivery of the peptide include orally, by encapsulation in microspheres or proteinoids, by aerosol delivery to the lungs, or transdermally by iontophoresis or transdermal electroporation. To administer a peptide of the invention by certain routes of administration, it can be necessary to coat the compound with, or co-administer the compound with, a material to prevent its inactivation. The method of the invention also includes delivery systems such as microencapsulation of peptides into liposomes or a diluent. Pharmaceutically acceptable diluents include saline and aqueous buffer solutions.

"Therapeutically effective amount" as used herein for treatment of antimicrobial related diseases and conditions refers to the amount of peptide used that is of sufficient quantity to decrease the numbers of bacteria, viruses, fungi, and parasites in the body of a subject. The dosage ranges for the administration of peptides are those large enough to produce the desired effect. The amount of peptide adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age, pharmaceutical formulation and concentration of active agent, and the like. In calculating the dosage regimen for a patient, the mode of administration also is taken into consideration. The dosage regimen must also take into consideration the pharmacokinetics, i.e., the pharmaceutical composition's rate of absorption, bioavailability, metabolism, clearance, and the like. The dosage regimen can be adjusted by the individual physician in the event of any contraindications.

Dosage regimens of the pharmaceutical compositions of the present invention are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

"Bactericidal amount" as used herein refers to an amount sufficient to achieve a bacteria-killing blood concentration in the subject receiving the treatment. The bactericidal amount of antibiotic generally recognized as safe for administration to a human is well known in the art, and as is known in the art, varies with the specific antibiotic and the type of bacterial infection being treated.

Because of the antibiotic, antimicrobial, and antiviral properties of the peptides, they may also be used as preservatives or sterilants of materials susceptible to microbial or viral contamination. The peptides of the invention can be utilized as broad spectrum antimicrobial agents directed toward various specific applications. Such applications include use of the peptides as preservatives in processed foods (organisms including *Salmonella, Yersinia*, and *Shigella*), either alone or in combination with antibacterial food additives such as lysozymes; as a topical agent (*Pseudomonas, Streptococcus*) and to kill odor producing microbes (*Micrococci*). The relative effectiveness of the peptides of the invention for the applications described can be readily determined by one of skill in the art by determining the sensitivity of any organism to one of the peptides.

Unless otherwise defined, all technical and scientific terms used herein have the same meaning as commonly understood by a person skilled in the art. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following particular embodiments and drawings are provided by way of illustration, and they are not intended to be limiting of the present invention. Furthermore, the present invention covers all possible combinations of particular and preferred embodiments described herein.

EXAMPLES

Materials and Strains

Figure 1:
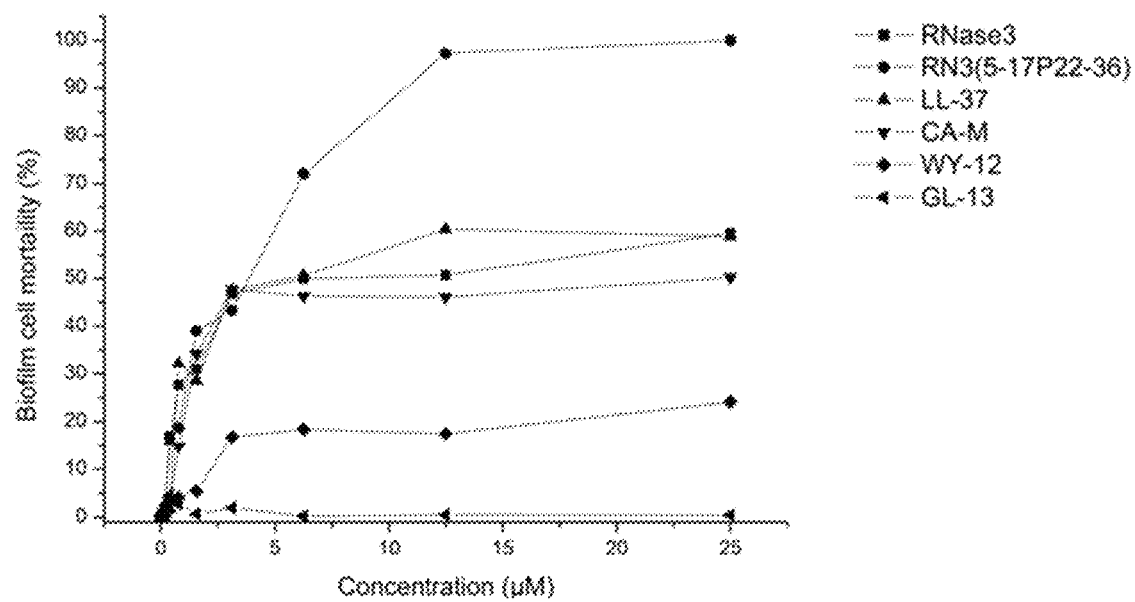
FIG. 1. Biofilm cell mortality by RNase 3, RN3(5-17P22-36), GL-13, LL-37, WY-12, CA-M on established *P. aeruginosa* biofilms assessed by the BactTiter-Glo™ luminescence assay.
Figure 2:
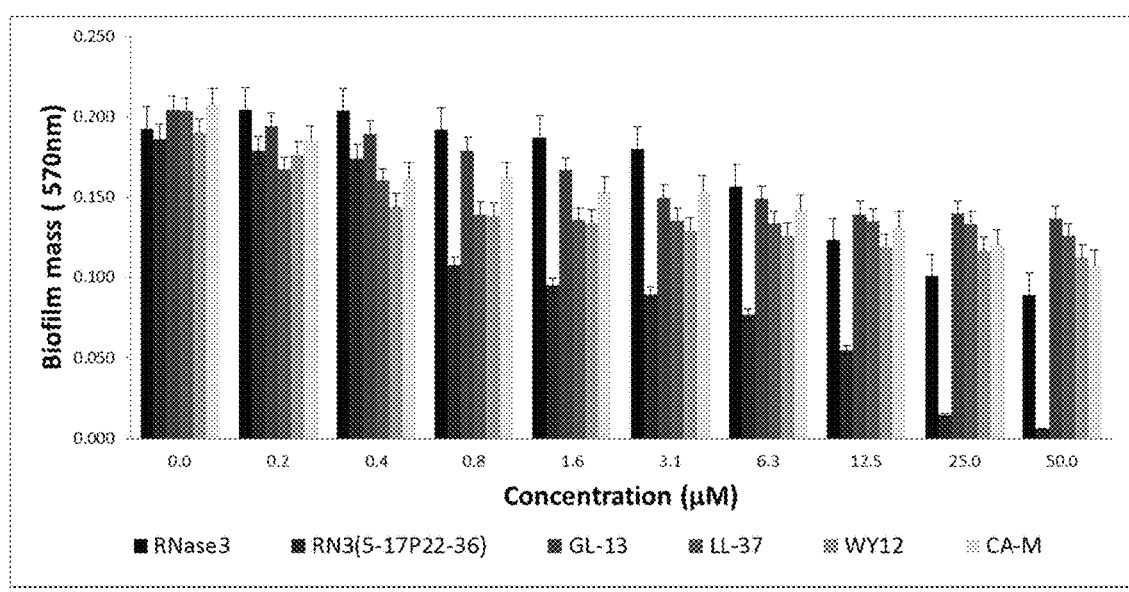
FIG. 2. Biofilm eradication by protein and peptides on established *P. aeruginosa* biofilms assayed by the crystal violet technique as described in the methodology.

BODIPY TR cadaverine (BC), where BODIPY is boron dipyrromethane (4,4-difluoro-4-bora-3a,4a-diaza-s-indacene) were purchased from Invitrogen (Carlsbad, Calif.). SYTOX Green was purchased from Invitrogen (Carlsbad, Calif.). LPS (lipopolysaccharides) from *P. aeruginosa*, Lectin from *Triticum vulgaris* (WGA), Crystal violet dye, FITC conjugated and 2-(4-Amidinophenyl)-6-indolecarbamidine dihydrochloride (DAPI) were purchased from Sigma-Aldrich (St. Louis, Mo.). The Alexa Fluor 488 protein labeling kit and the LIVE/DEAD bacterial viability kit were purchased from Molecular Probes (Eugene, Oreg.). The BacTiter-Glo™ assay kit was from Promega (Madison, Wis.). *E. coli* (BL21) was from Novagen (Madison, Wis.) and *Staphylococcus aureus* 502A (ATCC 27217). *Pseudomonas aeruginosa* PA01 (ATCC 15692) (Jacobs M. A. et al. 2003) was a kind gift from Dr. Isidre Gibert (Institut de Biotecnologia i Biomedicina, Universitat Autònoma de Barcelona, Cerdanyola del Vallès (Barcelona, Spain). Strains of *E. coli* NDM, *Acinetobacter baumannii* and *Acinetobacter multiresistent* were clinical isolates from the Hospital Vall d'Hebron (Barcelona). Fresh sheep red blood cells were purchased from Oxoid (Basingstoke, United Kingdom).

Protein and Peptides

Recombinant RNase 3 was expressed from a human synthetic gene cloned in pET11c. Protein expression in the *E. coli* BL21DE3 strain, folding of the protein from inclusion bodies, and purification were carried out as previously described (Boix E. et al. 1999).

All the peptides used in this work; the RNase 3 N-terminal derived peptides RN3(1-36) and RN3(5-17P22-36) and the antimicrobial reference peptides LL-37, CA-M, GL-13 and WY-12, all synthesized with C-terminal amidation, were acquired from Genecust (Dudelange, Luxembourg).

TABLE 1

Sequence information of the assayed antimicrobial peptides.

| Peptide | Amino acid sequence |
|---|---|
| RN3(5-17P22-36) | SEQ ID NO: 1:<br>RPFTRAQWFAIQHISPRTIAMRAINNYRWR-NH2 |
| RN3(1-36) | SEQ ID NO: 2:<br>RPPQFTRAQWFAIQHISLNPPRCTIAMRAINNYRWR-NH2 |
| GL-13 | SEQ ID NO: 3: GQIINLKASLDLL-NH2 |
| LL-37 | SEQ ID NO: 4:<br>LLGDFFRKSKEKIGKEFKRIVQRIKDFLRNLVPRTES-NH2 |
| WY12 | SEQ ID NO: 5: YVLWKRKRFIFI-NH2 |
| CA-M | SEQ ID NO: 6: KWKLFKKIGIGAVLKVLTTGLPALIS-NH2 |

TABLE 2

Chemical properties of the assayed antimicrobial peptides

| Peptide | MW (Da) | Net charge at pH 7 | Hydropathicity (GRAVY scale) |
|---|---|---|---|
| RN3(1-36) | 4411.1 | +7 | −0.6639 |
| RN3(5-17P22-36) | 3758.3 | +7 | −0.6667 |
| GL-13 | 1397.6 | +1 | +0.8000 |
| LL-37 | 4493.3 | +7 | −0.7243 |
| WY12 | 1669.0 | +5 | +0.3000 |
| CA-M | 2795.5 | +6 | +0.8423 |

Example 1

Antimicrobial Action on Planktonic *P. aeruginosa*

First the peptide ability to inhibit the proliferation of *P. aeruginosa* cells was assessed by determining the minimum inhibitory concentration ($MIC_{100}$). All the antimicrobial peptides (AMPs) under investigation were able to inhibit the microbial growth at a micromolar range, except for the GL-13 peptide, which showed no bacterial inhibition even at the maximum tested concentration (50 µM). In particular, RNase 3 and the N-terminus peptide RN3(5-17P22-36) were the most active compounds displaying MIC values about 2.5 µM, followed by the well-known antimicrobial peptides LL-37 and CA-M that produced the same microbial inhibition with concentrations two fold higher. Lastly, the antimicrobial peptide WY-12 needed more than 10 µM to totally inhibit *P. aeruginosa* growth (Table 3).

Minimum Inhibitory Concentration (MIC) Assay: Antimicrobial activity was calculated as the minimum inhibitory concentration ($MIC_{100}$), defined as the lowest protein/peptide concentration that completely inhibits microbial growth. $MIC_{100}$ of each protein/peptide was determined as described (Torrent M. et al. 2012). Bacteria were incubated at 37° C. overnight in Luria-Bertani broth (LB) and diluted to give approximately $5 \times 10^5$ CFU/mL. In each assay protein/peptide serially diluted from 50 to 0.2 µM in 10 mM sodium phosphate, 0.1 M NaCl, buffer pH 7.5 were added to 100 µl bacteria dilution and incubated for 4 h at 37° C. Subsequently, samples were plated onto Petri dishes and incubated at 37° C. overnight. $MIC_{100}$ values were determined as function of the total growth inhibition by the protein and peptides, from two independent experiments performed in triplicate.

Example 2

Microbial Cell Viability

The microbial cell viability was then assayed using the BacTiter-Glo™ luminescent kit. Viable *P. aeruginosa* cells metabolically active were measured by ATP quantification using a coupled luciferin/oxyluciferin in the presence of luciferase, where luminescence is proportional to ATP and hence to the number of viable cells in the culture. Results (Table 3) highlighted RNase 3 as the most active compound with IC50s values below 1 µM, followed by RN3(5-17P22-36), followed by LL-37, CA-M and WY-12, that needed respectively increasing concentrations to reduce cell viability to 50%. No cell reduction was detected for the peptide GL-13 even for the maximum concentration assayed (50 µM).

Bacterial Cell Viability Luminescent Assay:

Bacterial viability was assayed using the BacTiter-Glo™ microbial cell viability kit. Briefly, protein/peptides were dissolved in 10 mM sodium phosphate, 0.1M buffer, pH 7.5, serially diluted from 50 to 0.1 µM and tested in a 96-well microtiter plate containing *P. aeruginosa* planktonic ($OD_{600}$~0.2) or 24 h formed biofilm for 4 h at 37° C. Fifty microliters of BacTiter-Glo™ reagent was added to each well according to the manufacturer's instructions and incubated at room temperature for 15 min. Luminescence was read on a Victor3 plate reader with a 3-s integration time. Fifty percent ($ED_{50}$) and total inhibitory concentrations were calculated by fitting the data to a dose-response curve.

Example 3

Agglutination Activity

Bacterial agglutination of RNase 3 is important for the antimicrobial activity of the protein. Therefore, the peptide capability to agglutinate *P. aeruginosa* cells was assayed by the minimum agglutination concentration assay (MAC) (Table 3). As described before for other Gram-negative species, RNase 3 was able to agglutinate *P. aeruginosa* in a micromolar range. Interestingly, the peptide RN3(5-17P22-36) displayed an even lower MAC value producing bacterial agglutination at 1.5 µM. In addition, the peptide GL-13 was able to agglutinate *P. aeruginosa* in a submicromolar range, as previously described (Gorr U. et al. 2008) devoid however of any antimicrobial activity. Finally, LL-37, CA-M and WY-12 were not able to produce any bacterial agglutination.

Minimum Agglutination Activity (MAC):

Bacterial cells were grown in LB at 37° C. to an $OD_{600}=0.2$, centrifuged at 5000×g for 2 min and resuspended in 10 mM Tris-HCl buffer, 0.1 M NaCl, pH 7.5. An aliquot of 100 µl of the bacterial suspension was treated with increasing protein/peptide concentrations (from 0.01 to 50 µM) and incubated at room temperature for 1 h. The aggregation behavior was observed by visual inspection and the agglutinating activity is expressed as the minimum agglutinating concentration of the sample tested, as previously described (Torrent M. et al. 2012).

TABLE 3

Antimicrobial and agglutinating activities of RNase 3, RN3(5-17P22-36) and reference peptides GL-13, LL-37, WY-12, CA-M on planktonic *P. aeruginosa*. The 100% MIC ($MIC_{100}$), the 50% bacterial viability ($IC_{50}$), and the minimum agglutinating activity (MAC) were calculated as described in EXAMPLES 1, 2 and 3. N.D.: not detected at the maximum assayed concentration (50 µM). Values are indicated as mean ± SEM.

| | $MIC_{100}$ (µM) | $IC_{50}$ (µM) | MAC (µM) |
|---|---|---|---|
| RNase 3 | 2.50 ± 0.05 | 0.84 ± 0.03 | 2.00 ± 0.15 |
| RN3(5-17P22-36) | 2.50 ± 0.08 | 1.25 ± 0.10 | 1.50 ± 0.08 |
| GL-13 | >50 | N.D. | 0.70 ± 0.05 |
| LL-37 | 6.00 ± 0.05 | 2.28 ± 0.22 | >50 |
| WY-12 | 12.50 ± 0.12 | 7.72 ± 0.37 | >50 |
| CA-M | 6.00 ± 0.05 | 2.54 ± 1.08 | >50 |

Example 4

LPS Binding Affinity

Following, LPS binding affinity was monitored by a fluorometric assay which measures the competitive displacement of a cadaverine fluorescent probe (BC) by the protein and peptides. The half LPS binding affinity ($ED_{50}$), defined as the AMP concentration needed to achieve half of BC displacement, and the total LPS binding affinity, expressed as a percentage, were determined (Table 4). Interaction with negatively charged surfaces of bacteria is the first step for cationic peptides to reach the bacterial membranes and exert their antimicrobial action. All tested peptides were able to displace the fluorescent BC probe in a micromolar range, confirming LPS interaction. It is worth noticing that RN3(5-17P22-36), together with LL-37 and WY-12, achieved the total displacement of the BC molecule in the assayed conditions.

LPS Binding Assay:

LPS binding was assessed using the fluorescent probe BODIPY TR cadaverine (BC) as previously described (Pulido D. et al. Febs J 2013). BC binds strongly to native LPS, specifically recognizing the lipid A portion. When a protein that interacts with LPS is added, BC is displaced from the complex and its fluorescence is increased, decreasing its occupancy factor. LPS-binding assays were carried out in a 10 mM Hepes buffer at pH 7.5. The displacement assay was performed using a 96 well microtiter plate containing stirred mixture of either LPS (10 µg/mL) and BC (10 µM). Protein/peptides were serially diluted from 10 to 0.1 µM. Fluorescence measurements were performed on a Victor3 plate reader (Perkin Elmer, Waltham, Mass.). The protein/peptide concentration required to achieve half of total and total BC displacement was estimated from nonlinear regression analysis as previously described (Wood S. J. et al. 2004)

TABLE 4

LPS binding of RNase 3, RN3(5-17P22-36), GL-13, LL-37, WY-12, CA-M. The effective concentration for 50% displacement ($ED_{50}$) and the percentage of maximum displacement were calculated as described in EXAMPLE 4. 100% refers to a total displacement whereas 0% is for no displacement of the dye, indicating no binding. Values are indicated as mean ± SEM.

| | LPS binding | |
|---|---|---|
| | $ED_{50}$ (µM) | $\%_{max}$ |
| RNase 3 | 1.79 ± 0.32 | 99.85 ± 9.51 |
| RN3(5-17P22-36) | 2.11 ± 0.12 | 92.16 ± 2.06 |
| GL-13 | 1.63 ± 0.11 | 44.37 ± 3.84 |
| LL-37 | 2.65 ± 0.11 | 100.00 ± 3.13 |
| WY-12 | 2.90 ± 0.02 | 99.08 ± 0.50 |
| CA-M | 5.69 ± 0.89 | 69.16 ± 6.23 |

Example 5

Ability to Depolarize *P. aeruginosa* Membranes

To further investigate the antimicrobial mechanism of action of the peptide, its ability to depolarize *P. aeruginosa* membranes was evaluated. Depolarization activity was analyzed by the DiSC3(5) assay (Table 5). DiSC3(5) is a fluorescent probe, which is sensitive to membrane potential. The DiSC3(5) fluorescence is quenched upon interaction with intact cell membranes. When the membrane potential is lost, the probe is released to the medium, resulting in an increase of fluorescence that can be recorded as a function of peptide concentration. Thus, the half depolarization action ($ED_{50}$) was evaluated, defined as the peptide concentration needed to achieve a half-depolarization effect, and the total depolarization activity at final incubation time (Table 3). All the AMPs tested were able to depolarize *P. aeruginosa* cytoplasmic membrane in a micromolar range except for the peptide GL-13, which was not able to produce any depolarization effect under the concentrations tested. Moreover, RNase 3 and its N-terminus derived peptide RN3(5-17P22-36) were able to achieve close to total depolarization of the *P. aeruginosa* population; showing even higher values than the antimicrobial peptide CA-M, which is frequently used as a positive control due to its high depolarization effect.

Bacteria Cytoplasmic Membrane Depolarization Assay:

Membrane depolarization was followed using the method described earlier (Torrent M. et al. 2008). Briefly, bacterial cells were grown at 37° C. to an $OD_{600}=0.2$, centrifuged at 5000×g for 7 min, washed with 5 mM Hepes at pH 7.2 containing 20 mM glucose, and resuspended in 5 mM Hepes-KOH, 20 mM glucose, and 100 mM KCl at pH 7.2 to an $OD_{600}=0.05$ and 200 µl were transferred to a microtiter plate for planktonic assays. For biofilm assay, 24 h formed *P. aeruginosa* biofilm in a 96-well microtiter plate were washed three times with sterile PBS. Afterwards *P. aerugi-* nosa biofilms were washed with 5 mM Hepes at pH 7.2 containing 20 mM glucose, and rinsed in 5 mM Hepes-KOH, 20 mM glucose, and 100 mM KCl at pH 7.2. In both cases, DiSC3(5) was added to a final concentration of 0.4 µM and changes in the fluorescence were continuously recorded after addition of peptides at 10 µM in a Victor3 plate reader. A maximum reference value for total depolarization is calculated for Triton X-100 at 10%. Alternatively, changes in the fluorescence were continuously recorded after addition of a serially diluted protein/peptides from 50 to 0.1 µM. The peptide concentration required to achieve half of total and total membrane depolarization after 40 min incubation time was estimated from nonlinear regression analysis as previously described (Torrent M. et al. 2010)

Example 6

Membrane-Permeabilization Activity

Further insight into the membrane-permeabilizing effect of the selected AMPs against *P. aeruginosa* was evaluated by the Sytox Green assay. Local membrane disturbances allow the cell uptake of the fluorescent Sytox Green dye that subsequently stains the cell nucleic acids; the fluorescence increase is registered to monitor the cell membrane permeabilization. Therefore, the half permeabilization action ($ED_{50}$) was measured, and the total permeabilization activity expressed as a percentage (Table 5). All the studied AMPs were able to permeabilize *P. aeruginosa* cytoplasmic membrane in a micromolar range; with the exception of GL-13, which was unable to perform any cell membrane permeabilization under the concentrations tested. RNase 3 was the most active compound with an $ED_{50}$ below 1 µM, RN3(5-17P22-36) and LL-37 peptides needed approximately to double this concentration to exert half of their permeabilizing effect. On the other hand, WY-12 and CA-M required a 6- to 7-fold greater concentration than RNase 3 to produce half of their permeabilizing effect. Regarding to the total permeabilizing effect it is important to highlight that RNase 3 and the RN3(5-17P22-36) peptide showed the best total permeabilization values.

SYTOX Green Fluorescence Membrane Permeabilization Assay:

Membrane permeabilization was followed using the method SYTOX Green Fluorescence membrane permeabilization assay. In the planktonic assay, bacterial cells were grown at 37° C. to an $OD_{600}$=0.2, centrifuged at 5000×g for 5 min, and resuspended in 1×PBS to an $OD_{600}$=0.2. An aliquot of 200 µl was then transferred to a microtiter plate. For biofilm assay, 24 h formed *P. aeruginosa* biofilm in a 96-well microtiter plate were washed three times with sterile PBS. SYTOX Green was added to a final concentration of 1 µM and incubated 15 min in darkness. Changes in the fluorescence were continuously recorded after addition of a serially diluted protein/peptides from 50 to 0.1 µM in a Victor3 plate reader. The peptide concentration required to achieve half of total and total membrane permeabilization achieved after 40 min was estimated from nonlinear regression analysis as previously described (Pulido D. et al. Antimicrob Agents Chemother 2013). A maximum reference value was taken for Triton X-100 at 10%.

TABLE 5

Membrane permeabilization, and membrane depolarization activities of RNase 3, RN3(5-17P22-36), GL-13, LL-37, WY-12, CA-M on planktonic *P. aeruginosa*. Depolarization and permeabilization activities were calculated as described in EXAMPLES 5 and 6. The peptide concentration required to achieve half of total activity and the mean percentage of maximum activity were registered. The percentages were calculated taking 10% Triton X-100 as the maximum reference value. N.D.: not detected at the maximum assayed concentration (50 µM). Values are indicated as mean ± SEM.

| | Depolarization | | Permeabilization | |
|---|---|---|---|---|
| | $ED_{50}$ (µM) | %$_{max}$ | $ED_{50}$ (µM) | %$_{max}$ |
| RNase 3 | 1.54 ± 0.06 | 80.03 ± 2.67 | 0.92 ± 0.17 | 45.67 ± 2.29 |
| RN3(5-17P22-36) | 1.26 ± 0.03 | 78.19 ± 6.33 | 1.67 ± 0.90 | 63.63 ± 1.42 |
| GL-13 | N.D. | N.D. | N.D. | N.D. |
| LL-37 | 1.31 ± 0.01 | 28.24 ± 2.91 | 2.20 ± 0.23 | 38.80 ± 1.13 |
| WY-12 | 4.23 ± 0.21 | 44.02 ± 4.01 | 7.18 ± 1.15 | 39.43 ± 1.19 |
| CA-M | 3.01 ± 0.31 | 71.36 ± 7.60 | 6.11 ± 0.58 | 34.69 ± 2.18 |

Example 7

Antimicrobial Action on *P. aeruginosa* Biofilms

As a first approach, the biofilm cell viability was monitored using the BacTiter-Glo™ luminescent assay. Therefore, the antimicrobial action of the studied AMPs was determined on already established *P. aeruginosa* biofilms (FIG. 1 and Table 6). All the AMPs tested were able to exert their bactericidal action in a micromolar range; with the exception of GL-13, which was unable to perform any cell mortality even at the maximum tested concentration (50 µM). However, for all the active peptides, the concentrations needed to produce an equivalent effect in biofilms were between 2 to 10 times higher than in planktonic cultures. Interestingly, we determined that the only AMP that could reduce the bacterial population on the established biofilm on its totality was the RN3(5-17P22-36), showing even better results than the parental protein, which achieved a cell death percentage close to 50. At the same time, we applied the crystal violet technique to assess the peptide ability to disperse pre-established *P. aeruginosa* biofilms.

Following, the biofilm eradication activity was determined (FIG. 1 and Table 6). Analysis of the biofilm eradication effect revealed that RNase 3 displayed a high anti-biofilm effect achieving values higher than 60%. Interestingly, its derived N-terminal peptide RN3(5-17P22-36) presented a higher biofilm eradication activity than its parental protein, being able to totally disperse the cell community layer. On the other hand, the reference peptides LL-37, CA-M, WY-12 and GL-13 showed moderate effects being able to disperse from 30 to 50% of the total biofilm. Moreover, the biofilm eradication activity of all the tested reference peptides was well above the maximum concentration tested (50 µM), except for RN3(5-17P22-36) which was able to eradicate the biofilm close to 50 µM.

Biofilm Formation:

Biofilm formation assay was modified from the previously described protocol (Huedo P. et al. 2014). Briefly, overnight cultures of *P. aeruginosa* were centrifuged at 5000×g for 5 min, washed and adjusted to an $OD_{600}$=0.1 in tryptic soy medium (TSB). Two hundred microliters of the bacterial suspension were dispensed in each well of a polystyrene 96-well microtiter plate (Greiner Bio-one, France). The plate was incubated at 37° C. on an orbital shaker (30 rpm). The media was exchanged with fresh pre-warmed TSB after 4 h, in order to remove the non-attached bacteria. After 24 h incubation, the formation of biofilm was then evaluated using the crystal violet staining technique (Stepanovic S. et al. 2000). Briefly, the plates were washed three times with PBS, fixed at 60° C. for 1 h, and stained for 15 min with 200 µl of 0.1% crystal violet. After the dye was discarded, plates were rinsed in PBS and allowed to dry for 30 min at 37° C. Crystal violet was dissolved in 250 µl of 95% ethanol for 15 min, and the $OD_{570}$ of the extracted dye was measured using a Victor3 plate reader (Perkin-Elmer, Waltham, Mass.).

Biofilm Eradication Assay:

Biofilms were grown as above. Twenty-four hour formed P. aeruginosa biofilm was washed three times with sterile PBS, and rinsed with 10 mM sodium phosphate buffer pH 7.5. Each well was treated with increasing protein/peptide concentrations (from 0.01 to 50 µM) and incubated at 37° C. for 4 h. The biofilm eradication was then evaluated using the crystal violet staining technique (Stepanovic S. et al. 2000). The ability of the antimicrobial peptides to disperse and reduce the biofilm mass of preformed biofilms was calculated. The peptide concentration required to achieve total preformed biofilm eradication after 4 h incubation time was estimated. A maximum reference value was taken for Triton X-100 at 10%. The minimum biofilm eradication concentration (MBEC), defined as the protein/peptide concentration where the 99.9% of the biofilm mass is eradicated was estimated.

TABLE 6

Biofilm eradication and mortality activities of RNase 3, RN3(5-17P22-36), GL-13, LL-37, WY-12, CA-M on pre-established P. aeruginosa biofilm. The mean percentage value for maximum activity was calculated for biofilm eradication and cell mortality activities as described in EXAMPLE 7, taking 10% Triton X-100 as the maximum reference value. N.D: not detected at the maximum assayed concentration (50 µM). Values are indicated as mean ± SEM.

|   | Biofilm eradication ($\%_{max}$) | Biofilm cell mortality ($\%_{max}$) |
|---|---|---|
| RNase 3 | 63.29 ± 4.08 | 67.31 ± 0.79 |
| RN3(5-17P22-36) | 100.00 ± 5.00 | 96.40 ± 2.41 |
| GL-13 | 33.28 ± 1.07 | N.D. |
| LL-37 | 35.54 ± 1.13 | 64.05 ± 3.33 |
| WY-12 | 38.36 ± 2.36 | 39.67 ± 8.93 |
| CA-M | 53.03 ± 1.46 | 54.32 ± 5.51 |

Example 8

Biofilm Cell Membrane Depolarization and Permeabilization Activity Against Established P. aeruginosa Biofilms Thereupon, the antimicrobial mechanism of action of the RNase 3 derived peptide on P. aeruginosa biofilms was further characterized with the depolarization and permeabilization assays. As applied for the P. aeruginosa planktonic culture, the fluorescent DisC3(5) assay was also used here in order to monitor the depolarization activity of the studied protein and peptides against established biofilms. Therefore, we have measured the half depolarization action ($ED_{50}$), and the total depolarization activity expressed as a percentage (Table 7). Results indicated that the biofilm structure hinders the depolarization activity of the studied AMPs; where the depolarization activity of all the peptides tested was reduced by 2 to 3-fold when compared to the effect in the planktonic P. aeruginosa culture. Similar results were obtained for the Sytox Green permeabilization assay, where the total permeabilization effect was hindered for all the AMPs tested, and between two to ten times higher concentrations were required to achieve half of the biofilm cell permeabilizing effect in comparison to the planktonic cells. Nevertheless, the highest mean percentage values at final incubation time were achieved for the RN3(5-17P22-36) peptide.

TABLE 7

Biofilm cell membrane depolarization and permeabilization activities of RNase 3, RN3(5-17P22-36), GL-13, LL-37, WY-12, CA-M on established P. aeruginosa biofilms. Maximum percentage at final incubation time calculated as mean value ($\%_{max}$) and the peptide concentration required to achieve half of total activity (ED50) for depolarization and permeabilization activities were calculated as described in EXAMPLES 5 and 6, taking 10% Triton X-100 as the maximum reference value. N.D.: not detected at the assayed concentration range (50 µM). Values are indicated as mean ± SEM.

|   | Depolarization | | Permeabilization | |
|---|---|---|---|---|
|   | $ED_{50}$ (µM) ± SEM | Mean % ± SEM | $ED_{50}$ (µM) ± SEM | Mean % ± SEM |
| RNase 3 | 9.45 ± 0.97 | 46.11 ± 3.21 | 8.59 ± 1.70 | 39.4 ± 2.88 |
| RN3(5-17P22-36) | 3.69 ± 0.37 | 73.51 ± 1.94 | 6.60 ± 2.01 | 64.26 ± 5.44 |
| GL-13 | N.D. | N.D. | N.D. | N.D. |
| LL-37 | 8.83 ± 0.54 | 31.85 ± 1.15 | 12.35 ± 3.13 | 24.21 ± 3.71 |
| WY-12 | 18.11 ± 0.89 | 32.58 ± 1.87 | 18.79 ± 8.23 | 18.91 ± 2.23 |
| CA-M | 15.79 ± 0.77 | 39.09 ± 2.46 | 10.64 ± 0.11 | 23.01 ± 1.13 |

Example 9

Hemolysis

Peptide hemolysis was estimated as previously described (Torrent M. et al. 2011). Fresh sheep red blood cells (RBCs) were washed three times with PBS (35 mM phosphate buffer, 0.15 M NaCl, pH 7.4) by centrifugation for 5 min at 3000×g and resuspended in PBS at 2×10$^7$ cells/ml. RBCs were incubated with peptides at 37° C. for 4 h and centrifuged at 13000×g for 5 min. The supernatant was separated from the pellet and its absorbance measured at 570 nm. The 100% hemolysis was defined as the absorbance obtained by sonicating RBCs for 10 s. Concentration required to achieve 50% hemolysis ($HC_{50}$) was calculated by fitting the data to a sigmoidal function.

$HC_{50}$ values estimated for both RNase 3 and the peptide are higher than 100 µM, providing high therapeutic indexes.

Example 10

Additionally other bacterial strains were assayed for their antimicrobial action following the assays described above, achieving $MIC_{100}$ values around 1 µM for Acinetobacter baumannii, E. coli NDM and Acinetobacter multiresistent and 0.2 µM for Staphylococcus aureus.

BIBLIOGRAPHIC REFERENCES

Torrent M. et al. "Refining the Eosinophil Cationic Protein Antibacterial Pharmacophore by Rational Structure Minimization" Journal of Medicinal Chemistry 2011, vol. 54, p. 5237-5244.

Kowalczyk W. et al. "Synthesis of multiple antigenic peptides (MAPs)-strategies and limitations" J of Pept Sci 2011, vol. 17, p. 247-251

Nagant C. et al., "Identification of peptides derived from the human antimicrobial peptide LL-37 active against biofilms formed by Pseudomonas aeruginosa using a library of truncated fragments" Antimicrob Agents Chemother 2012, vol. 56, p. 5698-5708.

Saugar J. M. et al. "Activity of cecropin A-melittin hybrid peptides against colistin-resistant clinical strains of Acinetobacter baumannii: Molecular basis for the differential mechanisms of action" Antimicrobial Agents and Chemotherapy 2006, vol. 50, p. 1251-1256.

Bhunia A. et al., "Designed beta-boomerang antiendotoxic and antimicrobial peptides: structures and activities in lipopolysaccharide" J Biol Chem 2009, vol. 284, p. 21991-22004.

Gorr S. U. et al., "Design of bacteria-agglutinating peptides derived from parotid secretory protein, a member of the bactericidal/permeability increasing-like protein family" Peptides 2008, vol. 29, p. 2118-2127.

Jacobs M. A. et al. "Comprehensive transposon mutant library of Pseudomonas aeruginosa" Proc Natl Acad Sci USA 2003, vol. 100, p. 14339-14344.

Boix E. et al. "Kinetic and product distribution analysis of human eosinophil cationic protein indicates a subsite arrangement that favors exonuclease-type activity" J Biol Chem 1999, vol. 274, p. 15605-15614.

Torrent M. et al. "Exploring new biological functions of amyloids: bacteria cell agglutination mediated by host protein aggregation" Plos Pathogens 2012, vol. 8, p. e1003005.

Pulido D. et al. "Towards the rational design of antimicrobial proteins: single point mutations can switch on bactericidal and agglutinating activities on the RNase A superfamily lineage" FEBS J 2013, vol. 280, p-5841-5852.

Wood S. J. et al. "Anti-endotoxin agents. 2. Pilot highthroughput screening for novel lipopolysaccharide-recognizing motifs in small molecules" Comb Chem High Throughput Screen 2004, vol. 7, p. 733-747.

Torrent M. et al. "Eosinophil cationic protein high-affinity binding to bacteria-wall lipopolysaccharides and peptidoglycans" Biochemistry 2008, vol. 47, p. 3544-3555.

Torrent M. et al. "Comparison of human RNase 3 and RNase 7 bactericidal action at the Gram-negative and Grampositive bacterial cell wall" Febs J 2010, vol. 277, p. 1713-1725.

Pulido D. et al. "Two human host defense ribonucleases against mycobacteria, the eosinophil cationic protein (RNase 3) and RNase 7" Antimicrob Agents Chemother 2013, vol. 57, p. 3797-3805.

Huedo P. et al. "Two different rpf clusters distributed among a population of Stenotrophomonas maltophilia clinical strains display differential diffusible signal factor production and virulence regulation" J Bacteriol 2014, vol. 196, p. 2431-2442.

Stepanovic S. et al. "A modified microtiter-plate test for quantification of staphylococcal biofilm formation" J Microbiol Methods 2000, vol. 40, p. 175-179.

The invention claimed is:

1. A peptide consisting of the amino acid sequence:

$X_1$-Pro$_2$-$X_3$-$X_4$-$X_5$-Ala$_6$-Gln$_7$-Trp$_8$-Phe$_9$-Ala$_{10}$-Ile$_{11}$-Gln$_{12}$-His$_{13}$-Ile$_{14}$-$X_{15}$-Pro$_{16}$-$X_{17}$-$X_{18}$-$X_{19}$-Ala$_{20}$-Met$_{21}$-$X_{22}$-Ala$_{23}$-Ile$_{24}$-$X_{25}$-$X_{26}$-Tyr$_{27}$-Arg$_{28}$-Trp$_{29}$-Arg$_{30}$-$X_{31}$-NH2, wherein:

$X_1$, $X_5$, $X_{17}$, $X_{22}$ are amino acids selected from the group consisting of Arg and Lys;

$X_3$ is an amino acid selected from the group consisting of Phe, Leu, Ile and Val;

$X_4$ is an amino acid selected from the group consisting of Thr, Phe and Ile;

$X_{15}$ is any amino acid;

$X_{18}$ is an amino acid selected from the group consisting of Thr, Ser, Gln and Asn;

$X_{19}$ is an amino acid selected from the group consisting of Ile, Leu and Val;

$X_{25}$ is an amino acid selected from the group consisting of Asn, His, and Lys;

$X_{26}$ is an amino acid selected from the group consisting of Asn, Lys and Trp; and $X_{31}$ is either absent or from one to nine amino acids selected from the group consisting of Asn, Gln, Ser and Thr.

2. The peptide according to claim 1, wherein the peptide has antimicrobial activity and has an inhibitory effect on biofilm formation by a biofilm-producing microorganism.

3. A peptide consisting of an amino acid sequence having a 90% identity to amino acid sequence SEQ ID NO: 1, wherein the peptide has antimicrobial activity and has an inhibitory effect on biofilm formation by a biofilm-producing microorganism.

4. The peptide according to claim 3, wherein the amino acid sequence is SEQ ID NO: 1.

5. An antimicrobial agent comprising the peptide according to claim 1.

6. An antibiofilm agent comprising the peptide according to claim 1.

7. A disinfectant for medical and surgical materials, the disinfectant comprising the peptide according to claim 1.

8. A medicament comprising the peptide according to claim 1.

9. A method for the treatment of an infectious disease in a subject in need thereof, the method comprising: administering an effective amount of the medicament according to claim 8 to the subject.

10. The method according to claim 9, wherein the infectious disease is selected from the group consisting of a bacterial, a viral, a parasitic and a fungal disease.

11. The method according to claim 10, wherein the infectious disease is a bacterial disease and is caused by a Gram negative bacterial pathogen.

12. The method according to claim 11, wherein the Gram negative pathogen is selected from the group consisting of: *Pseudomonas, Escherichia coli, Acinetobacter, Salmonella* and *Klebsiella*.

13. A pharmaceutical composition comprising:
the peptide according to claim 1; and
a pharmaceutically acceptable carrier, diluent or excipient.

14. A composition comprising,
the peptide according to claim 1; and
a carrier or diluent.

15. An item impregnated with, coated with or covered by a composition comprising the peptide according to claim 1, wherein the item is selected from the group consisting of a medical device, a medical instrument, a medical implement, a prosthetic, an implantable device or material, a wound dressing, and a biologically compatible material.

* * * * *

SEQUENCE LISTING

```
<160> NUMBER OF SEQ ID NOS: 7

<210> SEQ ID NO 1
<211> LENGTH: 30
<212> TYPE: PRT
<213> ORGANISM: Artificial
<220> FEATURE:
<223> OTHER INFORMATION: peptide RN3(5-17P22-36)

<400> SEQUENCE: 1

Arg Pro Phe Thr Arg Ala Gln Trp Phe Ala Ile Gln His Ile Ser Pro
1               5                   10                  15

Arg Thr Ile Ala Met Arg Ala Ile Asn Asn Tyr Arg Trp Arg
            20                  25                  30

<210> SEQ ID NO 2
<211> LENGTH: 36
<212> TYPE: PRT
<213> ORGANISM: Artificial
<220> FEATURE:
<223> OTHER INFORMATION: peptide RN3(1-36)

<400> SEQUENCE: 2

Arg Pro Pro Gln Phe Thr Arg Ala Gln Trp Phe Ala Ile Gln His Ile
1               5                   10                  15

Ser Leu Asn Pro Pro Arg Cys Thr Ile Ala Met Arg Ala Ile Asn Asn
            20                  25                  30

Tyr Arg Trp Arg
        35

<210> SEQ ID NO 3
<211> LENGTH: 13
<212> TYPE: PRT
```

```
<213> ORGANISM: Artificial
<220> FEATURE:
<223> OTHER INFORMATION: peptide GL-13

<400> SEQUENCE: 3

Gly Gln Ile Ile Asn Leu Lys Ala Ser Leu Asp Leu Leu
1               5                   10

<210> SEQ ID NO 4
<211> LENGTH: 37
<212> TYPE: PRT
<213> ORGANISM: Artificial
<220> FEATURE:
<223> OTHER INFORMATION: peptide LL-37

<400> SEQUENCE: 4

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
            35

<210> SEQ ID NO 5
<211> LENGTH: 12
<212> TYPE: PRT
<213> ORGANISM: Artificial
<220> FEATURE:
<223> OTHER INFORMATION: peptide WY 12

<400> SEQUENCE: 5

Tyr Val Leu Trp Lys Arg Lys Arg Phe Ile Phe Ile
1               5                   10

<210> SEQ ID NO 6
<211> LENGTH: 26
<212> TYPE: PRT
<213> ORGANISM: Artificial
<220> FEATURE:
<223> OTHER INFORMATION: peptide CA-M

<400> SEQUENCE: 6

Lys Trp Lys Leu Phe Lys Lys Ile Gly Ile Gly Ala Val Leu Lys Val
1               5                   10                  15

Leu Thr Thr Gly Leu Pro Ala Leu Ile Ser
            20                  25

<210> SEQ ID NO 7
<211> LENGTH: 12
<212> TYPE: PRT
<213> ORGANISM: Artificial
<220> FEATURE:
<223> OTHER INFORMATION: peptide ECP(7-13)(32-36)

<400> SEQUENCE: 7

Arg Ala Gln Trp Phe Ala Ile Asn Tyr Arg Trp Arg
1               5                   10
```